ary Examiner—Shep K. Rose

United States Patent [19]

Schreiber et al.

[11] 4,132,771

[45] Jan. 2, 1979

[54] WARM TWO TONE FLAVORED DENTIFRICE

[76] Inventors: Ronald S. Schreiber, 96-C Cedar La., Highland Park, N.J. 08904; Joseph R. Principe, 131-B Taylor Ave., East Brunswick, N.J. 08816

[21] Appl. No.: 827,295

[22] Filed: Aug. 24, 1977

[51] Int. Cl.$^2$ .......................... A61K 7/16; A61K 7/18
[52] U.S. Cl. .......................................... 424/52; 424/49
[58] Field of Search ..................................... 424/49–58

[56] References Cited

U.S. PATENT DOCUMENTS

| | | | |
|---|---|---|---|
| 3,250,680 | 5/1966 | Menkart et al. | 424/56 |
| 3,574,824 | 4/1971 | Echeandia et al. | 424/50 |
| 3,957,964 | 5/1976 | Grimm | 424/10 |
| 4,001,438 | 1/1977 | Marmo et al. | 424/49 X |
| 4,071,614 | 1/1978 | Grimm | 424/49 |

*Primary Examiner*—Shep K. Rose

[57] ABSTRACT

There is disclosed an anhydrous heat releasing, two toned flavored dentifrice which contains an anhydrous synthetic zeolite as the sole or major abrasive, a flavoring agent and a fluorine containing compound as the essential ingredients.

8 Claims, No Drawings

WARM TWO TONE FLAVORED DENTIFRICE

This invention relates to a novel anhydrous heat-releasing dentifrice capable of delivering a two tone flavor in the oral cavity, immediately upon contact therewith, as when brushing one's teeth, and containing zeolite as the sole or major polishing agent and a suitable flavor, and preferably a fluorine containing compound.

The prior art discloses self-heating cosmetic preparations as shown in U.S. Pat. No. 3,341,418 to Moses et al. Said patent discloses a two-part aqueous liquid composition, to be applied to the skin as a shaving cream, or to the hair as a shampoo, packaged in a dual compartment container and to be simultaneously dispensed for exothermic reaction with each other, one compartment containing an oxidant such as hydrogen peroxide or the like in an aqueous medium and the other compartment containing a reducing agent such as thiourea and the like in an aqueous medium.

U.S. Pat. No. 3,250,680 to Menkart et al. also discloses a heat-generating cosmetic composition adapted to evolve heat when it contacts moisture which is an anhydrous composition containing about 5 to 40% of an anhydrous adsorbent material such as alkali metal alumino-silicate molecular sieves dispersed in a non-aqueous cosmetically-acceptable vehicle such as mineral oil or liquid polyalkylene glycol. The cosmetic compositions disclosed herein include skin and hand creams, shampoos and toothpaste. However, the toothpaste formula therein does not contain any flavoring agents nor is the sodium aluminum silicate the sole or major polishing agent. As a matter of fact, its content is less than that of each of the other two polishing agents. The presence of a flavoring agent which is totally absent in this patent is an essential ingredient in present novel dentifrice for its unusual and unexpected two-tone flavor in the mouth.

It has been observed that taste and flavor are perhaps the most important single aspects with respect to the consumer acceptance of a dentifrice formulation. The selection of acceptable sweetener and flavoring ingredients is therefore of significant importance in the formulation of a dentifrice. It has oftentimes been stated that the foregoing is both an art as well as a science. It is an art in the sense that it requires the blending of the various components with the flavoring agents such that the final composition contains a pleasing taste as well as provides a composition in which the flavor is stable. The foregoing has presented particular difficulties in incorporating flavoring agents in a dentifrice formulation inasmuch as the former must be compatible with the latter and remain essentially unchanged over the shelf life of the product. Some of those flavors which do not have stability problems have the drawback that they are not suitable for use due to the unacceptable timelag prior to the onset of their flavor and/or their associated side tastes. Inasmuch as dentifrices generally contain a detergent-like material, the sweetener employed therein must have the quality of a rapid onset of flavor so as to mask the generally bitter flavor associated with detergent-like ingredients. The use of low intensity flavors is, therefore, not practical for use in most dentifrice formulations. Merely increasing the amount of low intensity flavors so as to overcome the foregoing deficiencies does not prove very helpful inasmuch as a dentifrice generally contains large amounts of humectants, polishing agents, water and the like and therefore from a volume point of view, it is not practical.

The sensation of flavor is believed to be made up of taste received by the taste buds on the tongue, odors picked up by the olfactory mucosa of the nose as sensations, such as burning, cooling and astringency transmitted through the tactile nerve endings in the mouth. Flavor sensation is made up essentially of four basic tastes, sweet, sour, bitter and salty, which are registered by the taste buds on the tongue. Bitter flavors are detected by the back of the tongue, sweet at the tip, sour along the sides from midway to the back of the tongue and saltiness is detected more or less equally along the entire tongue.

Accordingly, it is an object of this invention to provide a dentifrice capable of effecting a unique and unusual flavor-odor sensation in the mouth by including a flavor in conjunction with an anhydrous synthetic zeolite as the essential polishing agent in an anhydrous formulation.

Another object of this invention is to provide an anhydrous dentifrice possessing a thermal effect in the oral cavity.

Accordingly, the present invention relates to an anhydrous heat releasing dentifrice which effects a two tone flavor change in the oral cavity consisting of a finely divided anhydrous synthetic zeolite having an appreciable heat of hydration and capable of being reversibly dehydrated as the sole or major polishing agent in amounts of about 10 to 50% by weight, about 0.1 to 5% by weight of at least one flavoring agent, and about 20 to 75% of an anhydrous liquid vehicle.

The synthetic zeolites useful herein are crystalline metal alumino silicates wherein the metal may be an alkali metal, an alkaline earth metal, zinc, copper or a mixture of metals and having an appreciable heat of hydration, and capable of being dehydrated and at least partially rehydrated without destroying the framework structure of the zeolite.

Zeolite has been defined by Smith, J. V., Mineralogical Society of America, Special Paper No. 1, 1963, as an alumino-silicate with a framework structure enclosing cavities occupied by large ions and water molecules, both of which have considerable freedom of movement permitting ion exchange and reversible dehydration.

A synthetic zeolite useful in this invention is typically commercially available from the Linde Division of Union Carbide Corporation, New York, New York as molecular sieves. These materials are fully described in U.S. Pat. Nos. 2,882,243 and 2,882,244. The structure of the A and X crystals may be represented as follows:

A-Crystal[$Na_{12}(AlO_2)_{12}(SiO_2)_{12}$]·$27H_2O$

X-Crystal[$Na_{86}(AlO_2)_{86}(SiO_2)_{106}$]·$264H_2O$

On heating, the water is removed leaving the crystal structure intact with an aluminum-oxygen-silicon structure.

The $AlO_2$ has one negative charge available for cation exchange. By making use of this property, the "pore size" can be varied.

The crystal symmetry of A-zeolites are cubic and the unit cell dimension is about 12.5 Å on each side. In the A-crystal the pores range from 3 to 5 Å and with the X-crystal from 8 to 12 Å. The X-crystal also has a cubic symmetry.

Molecules, if not too large, pass through the pores and are adsorbed on the inner surface and held by electrostatic forces. As materials are adsorbed in the sieves, more or less heat is evolved and in some cases where this energy is high, it causes the sieves to glow. The sieves rapidly take up the maximum amount of material (cavities full) and the partial pressure over the loaded sieve in some cases is very low.

The A-crystal with the small pore size is best suited for holding water and hence adapted to techniques and procedures where drying is the primary objective. The X-crystal with the larger pore size is usually preferred for loading since there is less limitation of the molecular size which can pass through the pore. Pore size affects the rate of displacement of adsorbed material but not the equilibrium.

The ability of the pores to pass certain molecules and exclude others has been the basis for a number of the present applications for separating similar compounds. For example, normal hydrocarbons readily pass through the pores whereas isohydrocarbons do not.

Materials adsorbed on the sieves may be released by heating, reduced pressure or by displacement by a more strongly adsorbed compound. For instance, water will remove any adsorbed material. The higher the molecular weight, the slower is the displacement by any means. Metal ions such as copper, zinc, alkali metals, magnesium, calcium and other alkaline earth metals are taken up or replaced in these sieves in accordance with the selectivity and capacity of each of these ions. However, the zeolites containing any of the aforementioned metal ions are equally effective in conjointly releasing heat and the adsorbed flavor components upon contact with water.

Commercially available synthetic zeolites are suitable for use as the sole or major dental polishing agent in instant dentifrice formulations and possess acceptable abrasivity for effective cleaning and polishing of the teeth, with the added advantage of releasing appreciable heat of hydration within the oral cavity substantially instantaneously so as to afford a pleasurable warm sensation which is coupled with an immediate flavor release, thereby eliminating any objectionable time lag prior to the onset of the flavored taste. Heat is evident in 30 seconds. The thermal effects are illustrated by the following tests, wherein 20 gms of dried zeolites were added to 80 gms deionized distilled water and the temperature recorded at intervals of minutes and seconds:

| Water temperature prior to addition: | | 24° C | 22° C | 22° C | 23° C |
|---|---|---|---|---|---|
| Zeolites added: | | Cu | Zn | 5A | SK40 |
| Minutes | Seconds | Temp° C | Temp° C | Temp° C | Temp° C |
| 0 | 30 | 25 | 34 | 38 | 37 |
| 1 | 0 | 28 | 34 | 39 | 36 |
| 1 | 30 | 30 | 34 | 39 | 36 |
| 2 | 0 | 31 | 34 | 38 | 35 |
| 2 | 30 | 31 | 33 | 38 | 35 |
| 3 | 0 | 31 | 33 | 37 | 35 |
| 5 | 0 | 30 | 32 | 35 | 34 |
| 8 | 0 | 29 | 30 | 33 | 33 |
| 10 | 0 | 28 | 29 | 33 | 32 |
| 15 | 0 | 27 | 28 | 30 | 30 |

Zeolites particularly useful herein include the molecular sieves named zeolite A which has the following properties:

A chemical composition defined heretofore, a cubic crystalline symmetry, the cell dimension being equal to 12.32 A (calculated for dehydrated zeolite), a density of 1.33 g/cc (calculated for dehydrated zeolite), a void volume of 0.3 cc/g (based on the amount of water contained per gram of dehydrated zeolite), and an aperture size of 4.2 Å;

Zeolite X which has the following properties: a chemical composition previously defined herein, a cubic crystalline symmetry, a cell dimension of 24.95 Å (dehydrated zeolite), a density of 1.29 g/cc (dehydrated zeolite), a void volume of 0.36 cc/g, and an aperture size of 8 Å;

Zeolite Y of the following chemical composition:

$$Na_{56}[(AlO_2)_{56}(SiO_2)_{136}]\cdot 264H_2O$$

which has a cubic symmetry and a cell dimension of 24.7 Å, a density of 1.30 g/cc (dehydrated), a void volume of 0.35 cc/g, and an aperture size of 8 Å;

Zeolite B of the following chemical composition:

$$Na_6[(AlO_2)_6(SiO_2)_{10}]\cdot 15H_2O$$

which is cubic in symmetry and has a cell dimension of 10.0 Å, a density of 1.47 g/cc (dehydrated), a void volume of 0.15 cc/g, and an aperture size of 3.5 Å;

Synthetic mordenite of the following chemical composition:

$$Na_8[(AlO_2)_8(SiO_2)_{40}]\cdot 24H_2O$$

which is orthorhombic in symmetry, has a density of 1.72 g/cc (dehydrated), has a void volume of 0.14 cc/g and an aperture size of 6.6 Å.

The above described zeolites may be varied by exchanging all or part of the sodium ions with other cations such as hydrogen and/or metal ions including the alkali metals, alkaline earth metals, zinc or copper or mixtures thereof.

The uniformity in composition and physical properties of the synthetic zeolites renders it particularly useful herein as opposed to natural occurring zeolites wherein the physical properties are non-uniform.

The synthetic zeolites can readily be dehydrated to remove substantially all the water by heating it in air or vacuum to temperatures up to 600° C., and preferably to a temperature of about 350° C. in a vacuum of $10^{-5}$ mmHg, without destroying the crystal structure thereof. Stability to heat has been observed up to temperatures of about 700° C. The proportion of anhydrous synthetic zeolite in the dentifrice may be from about 10 to 50% by weight and preferably about 20 to 35%.

The anhydrous synthetic zeolite has the property of generating heat of hydration when water is added thereto. Accordingly, the presence of said anhydrous zeolite in an anhydrous liquid vehicle containing a flavoring agent imparts a thermal effect in the oral cavity, as well as yields a unique and unusual flavor-odor sensation therein. More particularly, there is a sequential two tone flavor, a change in flavor, first a burst of one flavor which rapidly changes to another flavor. For example, when utilizing a single flavoring agent such as oil of peppermint in the zeolite containing dentifrice, the warmth due to the generation of heat in the oral cavity initially produced a burst of a cinnamon flavor which then tasted minty as the heat subsided. This change in flavor experience affords a pleasurable sensation and provides an unusual brushing experience. Thus, it is apparent that a variety of sequential two tone flavored dentifrices can be formulated by incorporating a single flavoring agent or a mixture of suitable flavoring agents.

Any suitable flavoring or sweetening sialagogues or mixture thereof may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon, lime, grapefruit and orange, as well as flavoring aldehydes, esters such as methyl salicylate, alcohols, and higher fatty compounds known in the art. Also useful are such chemicals as menthol, carvone and anethole. Of these, the most commonly employed are the oils of peppermint, spearmint, and eucalyptus and anethole, menthol and carvone. In some cases flavorful solvents, such as chloroform and mock chloroform, may be employed. Such flavorings may be used as liquids or may be solidified by being mixed with a particulate carrier material, such as starch, calcium carbonate, paraffin, vegetable wax, fat, higher fatty acid or other suitable carrier substances. In the cases of solid flavors, such as vanillin, sage, citric acid or licorice, the flavor may be converted to liquid form, if so desired, by dissolving it in the solvent or emulsifying it, usually with the help of a synthetic or natural emulsifying agent. The choice as to whether to utilize particulate solid or liquid flavors or to convert such flavors to a particulate solid or liquid form, respectively, will often depend on the properties desired in the flavor and its compatibility with the sweetener and any other material to be present with it. Suitable sweetening agents include mannitol, sucrose, lactose, maltose, sorbitol, xylitol, sodium cyclamate, saccharin, the dipeptides of U.S. Pat. No. 3,939,261 and the oxathiazin salts of U.S. Pat. No. 3,932,606. Suitably, flavor and sweetening agent may together comprise from about 0.1 to 10% or more of the compositions of the instant invention.

The compositions of the present invention preferably also contains a fluorine-containing compound having a beneficial effect on the care and hygiene of the oral cavity, e.g. diminution of enamel solubility in acid and protection of the teeth against decay. Examples thereof include sodium fluoride, stannous and manganese fluoride, potassium fluoride, potassium stannous fluoride ($SnF_2.KF$), sodium hexafluorostannate, stannous chlorofluoride, sodium or potassium fluorozirconate and sodium monofluorophosphate. These materials, which dissociate or release fluorine-containing ions in water, suitably may be present in an effective but non-toxic amount, usually within the range of about 0.01 to 1% by weight of the water soluble fluorine content thereof. Sodium fluoride and sodium monofluorophosphate are particularly preferred as well as mixtures thereof. The presence of the anhydrous zeolite which generates heat in the mouth enhances the fluoride action, thereby enhancing the anti-caries and anti-stain properties of the dentifrice.

In addition to enhanced fluoride pick-up and enhanced flavor sensation, the anhydrous zeolite containing dentifrice exhibits anti-odor activity as evidenced by an in vitro onion test, wherein 4 jars were filled with 1 gm onion. To each jar except one, was added 10 gms dried zinc loaded zeolite, 10 g dried copper loaded zeolite and 10 g anhydrous dicalcium phosphate, respectively, and stored. After 3 days the odors were evaluated by smelling the headspace in the jar and rating it from 1 to 4, with 4 being the pure onion odor and the control. An averge of 6 ratings per jar gave the following results:

| Jars | Additive | Odor rating |
|---|---|---|
| A | Zn zeolite | 2.4 |
| B | Cu zeolite | 1.1 |
| C | Dicalcium phosphate | 2.7 |
| D | None | 4.0 |

These results are indicative of enhanced anti-odor activity in comparison to dentifrices containing the conventional abrasives such as dicalcium phosphate.

The substantially anhydrous vehicle of this invention is preferably formulated from the following: (1) humectant or an oil; (2) gelling or binding agent; (3) standard toothpaste additives; and optionally, (4) water incompatible dentifrice additives, additional abrasives and inert ingredients.

The above-mentioned ingredients must, of course, be non-toxic and substantially anhydrous.

The dentifrice formulation of this invention includes liquids and solids that are proportioned as further defined hereinafter to form a creamy mass of desired consistency which is extrudable from an aerosol or other pressurized container or a collapsible tube (for example aluminum). In general, the liquids in the dental cream will comprise chiefly glycerine or an oil, propylene glycol, polyethylene glycol 400, etc., including suitable mixtures thereof. It is advantageous usually to use a mixture of both humectant and binder such as glycerine and Carbowax 600. The total liquid content will generally be about 20 to 75 percent by weight of the formulation. It is preferred to use also a gelling agent in dental creams and gels, such as the natural and synthetic gums and gum-like materials, for example, Irish moss, gum tragacanth, methyl cellulose, polyvinylpyrrolidone, hydrophilic colloidal carboxyvinyl polymers such as those sold under the trademark Carbopol 934 and 940, hydroxyethyl cellulose, Indian gum, acacia gums, agar agar, locust bean gum, synthetic silicated clays such as those sold under the trademark Laponite CP and Laponite SP, pectin and finely divided pyrogenic silica, sold under the trademarks Cab-O-Sil M5, Syloid 244, Syloid 266 and Aerosil D 200. The solid portion of the vehicle is usually present in an amount of up to about 10 percent and preferably about 0.2 to 5 percent by weight of the formulation.

The proportions of gelling agents or thickeners in the present dentifrices are sufficient to form an extrudable, shape-retaining product which can be squeezed from a tube onto a toothbrush and will not fall between the bristles of the brush but rather, will substantially maintain its shape thereon. In almost all cases no more than about 10% of gelling agent need be used and in most instances about 0.5 to 10% will suffice, and preferably about 1 to 5%.

Suitable oils for use in the practice of this invention include those which have viscosities ranging from about 100 to about 300 centipoises at 70° F., and can be mineral oil, light liquid petrolatum thickened to the necessary viscosity; and vegetable oils. The preferred mineral oil is Mineral Oil U.S.P. (also known as Liquid Petrolatum U.S.P., mineral oil (heavy medicinal), white mineral oil, liquid paraffin, and heavy liquid petrolatum). Mineral oil U.S.P. is defined in Remington's Pharmaceutical Sciences, 13th edition, Mack Publishing Co., Easton, Pa. 1965 as "a mixture of liquid hydrocarbons obtained from petroleum; a colorless transparent, oily liquid, free or nearly free from fluorescene". It is tasteless and odorless when cold and develops not more than a faint odor of petroleum when heated.

The preferred light liquid petrolatum is Light Liquid Petrolatum N.F. also known as light liquid paraffin and light white mineral oil. It is described in Remington's Pharmaceutical Sciences, as "... a mixture of liquid hydrocarbons obtained from petroleum, it may contain a stabilizer". If the Light Liquid Petrolatum N.F. is used as the oil it must be thickened to the required viscosity of from about 100 to about 300 centipoises at 70° F. with one of the well-known commercially available inert thickening materials, such as a pyrogenic silica sold under the trademark Cab-O-Sil, or a hydrogenated castor oil, sold under the tradename THIXIN.

Suitable vegetable oils which may be used as the oil ingredient include coconut oil, cotton-seed oil, sesame oil and similar non-toxic vegetable oils, as described in Vegetable Fats and Oils by E. W. Eckey, Reinhold Publishing Corp., New York, 1954. The vegetable oil selected must, of course, fall within the required viscosity range of from about 100 to about 300 centipoises. A particular vegetable oil falling within this range is NEOBFE M-5, a fractional triglyceride of coconut oil. It is desirable that the vegetable oil ingredient contain a minor amount of an antioxidant such as butylated hydroxyanisole or butylated hydroxytoluene, preferably in an amount ranging from about 0.1% to about 3% by weight, based on the weight of the vegetable oil employed.

The liquid vehicle of the dentifrice, together with the gelling agent(s) and other constituents, forms an extrudable mass of a non-dripping consistency when extruded from a collapsible tube, such as an aluminum tube. Thus, by the addition of more vehicle, the dental cream can be thinned and conversely, by the addition of more solids, especially more gelling agents, the products can be thickened. In most dentifrices, the liquid portion comprises glycerine. Although it is preferred to employ glycerine, other suitable vehicles in place thereof or in addition thereto may also be present, either with the mentioned polyhydric alcohols or in replacement for them. Thus, propylene glycol, polyethylene glycol, and polypropylene glycol may be employed providing that they are physiologically acceptable and produce products having a desired refractive index, in the case of the manufacture of visually clear dentifrices. Normally the proportion of vehicle is determined by the physical properties of the extrudate. Usually, however, from about 10 to 90% of the vehicle will be employed, with about 10 to 35% being a typical range for the production of opaque dentifrices and about 40 to 90% being useful for the manufacture of clear dental preparations.

It is to be understood that while ordinarily where sorbitol or mannitol is employed in a dentifrice, it is used as an aqueous solution, they may be employed herein, with the proviso, however, that it be substantially anhydrous (i.e., crystalline).

The preferred liquid vehicle is an anhydrous humectant or oil selected from the group consisting of glycerine, propylene glycol, polyethylene glycol, polypropylene glycol, liquid light petrolatum mineral oil, vegetable oil and suitable mixtures thereof.

The preferred gelling agents are selected from the group consisting of sodium carboxymethyl cellulose, hydroxyethyl cellulose, polyvinyl alcohol, Irish moss, silica aerogel or mixtures thereof.

In the preparation of tooth powders, it is usually sufficient to admix mechanically, e.g., by milling, the various solid ingredients, in appropriate quantities and particle sizes and thereafter carrying out procedures known in the art for containerization of the product.

In chewable dental tablets the solids and liquids are proportioned similarly to the amounts in dental creams and the flavor is blended with the solids and liquids, and a waxy matrix such as polyethylene glycol having a molecular weight of about 6,000 by weight, generally in amounts of about 4-20 percent by weight, in order to facilitate the formation of a tablet of the desired size and shape.

The formulation of this invention may optionally include an additional dentally acceptable, substantially water insoluble anhydrous polishing agent of the type commonly employed in dental creams. The polishing agents are usually finely divided water insoluble powdered materials. Preferably, they are from 1 to 40 microns, most preferably from 2 to 20 microns in particle sizes, with distribution of particle sizes being normal over the range. Representative polishing agents include, for example, dicalcium phosphate, tricalcium phosphate, insoluble sodium metaphosphate, aluminum hydroxide, colloidal silica, magnesium carbonate, calcium carbonate, calcium pyrophosphate, bentonite, etc., including suitable mixtures thereof. When employed, it is preferred to use a minor amount thereof, up to a maximum of 20% by weight of the formulation and preferably no more than 10%.

The above listing of polishing agents, and other listings of other constituents of the dentifrice composition to be given in the present specification are not intended to be exhaustive and therefore, for other materials of these types reference should be made to a standard handbook, such as Cosmetics: Science and Technology, by Sagarin, 2nd printing, 1963, published by Interscience Publishers, Inc.

Organic surface-active agents are used in the compositions of the present invention to assist in achieving thorough and complete dispersion of the instant compositions throughout the oral cavity and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitably such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2-dihydroxy propane sulfonates, and the substantially saturated high aliphatic acyl amides of lower aliphatic amino carboxylic acid compounds, such as those having 12 to 16 carbon atoms in the fatty acid, or acyl radicals, and the like. Examples of the last mentioned amides are N-lauroyl sarcosine, and the sodium potassium and ethanolamine salts of N-lauroyl, N-myristoyl, or N-palmitoyl sarcosine which should be substantially free from soap or similar higher fatty acid material which tends to substantially reduce the effect of these compounds. The use of these sarcosinate compounds in the dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface-active materials include nonionic agents such as condensates of sorbitan monostearate with approximately 20 moles of ethylene oxide, condensates of ethylene oxide with propylene oxide, condensates of propylene glycol ("Pluronics"), and amphoteric agents such as quaternized imidazole derivatives which are available under the trademark "Miranol" such as Miranol C₂M.

Other suitable nonionic detergents are the condensation products of an α-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant detergents are heteric polymers having a molecular weight in the range of 400 to about 1600 and containing 40% to 80% by weight of ethylene oxide, with an α-olefin to polyhydric alcohol mole ratio in the range of about 1:1 to 1:3. These detergents are manufactured using well-known polymerization techniques under conditions of high temperature and high pressure. The olefin oxide and polyhydric alcohol usually are added to the reactor prior to the addition of ethylene oxide. These nonionic detergents may be mixed with similar nonionic detergents as well as other types of nonionic detergents described therein.

There may also be employed olefin sulfonate detergents, typically long chain alkenyl sulfonates.

The α-olefin feedstock preferably contains olefins of 8-25 carbon atoms, most preferably 12-21 carbon atoms. The feedstock may contain minor amounts of other constituents, such as secondary or internal olefins, diolefins, cyclic olefins, aromatics, naphthalenes, and alkanes. Best results have been obtained when α-olefins (where $R_1$ is H) constitute a major proportion. A typical olefin feedstock contains in the range of about 12 to 21 carbon atoms in the molecule and yields olefin sulfonates having excellent detergency properties. Especially good foaming characteristics have been obtained by the use of a feedstock whose α-olefin content consists essentially of compounds of 15 to 18 carbon atoms.

The detergent material above produced, typically contains at least about 50% by weight of long-chain alkenyl sulfonate, up to about 33% by weight of hydroxy alkane sulfonate, and up to about 15% of impurities, such as long chain water-insoluble sultones, most of which impurities are characterized as being soluble in acetone.

The olefin sulfonate is generally employed in the form of its sodium salt. It is within the scope of this invention to use other water-soluble salts, for example, salts of other alkali metals such as potassium, salts of alkaline earth metals, such as magnesium and calcium, triethanolamine, salts and the like as well as mixtures of a salt such as a sodium salt with the free olefin sulfonic acid.

It is preferred to use from about 0.05 to 5% by weight and preferably about 0.5 to 5% of the foregoing surface-active materials in the instant oral preparations.

Various other compatible and suitable materials may be incorporated in the dentifrice formulations of this invention. Examples thereof are coloring or whitening agents or dyestuffs, preservatives, silicones, chlorophyll compounds, ammoniated materials such as urea, diammonium phosphate and mixtures thereof, and other constituents. These adjuvants are incorporated in the instant compositions in amounts which do not substantially adversely affect the properties and characteristics desired and are selected and used in proper amount depending upon the particular type of preparation involved.

Antibacterial agents may also be employed in the oral preparation of the instant invention to provide a total content of such agents of up to about 5% by weight, preferably about 0.01 to 5.0%, most preferably about 0.05 to 1.0%. Typical antibacterial agents include:

$N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
1,6-di-p-chlorophenyl biguanidohexane;
1,6-bis(2-ethylhexyl biguanido) hexane;
5-amino-1,3-bis(2-ethylhexyl)-5-methylhexahydropyrimidine;

and their non-toxic acid addition salts.

The dentifrice may be prepared by suitably mixing the ingredients. For instance in making a toothpaste, a gelling agent such as silica aerogel or Carbopol 934 and a preservative such as dried benzoic acid, if employed, fluoride and sweetener, if used, is dispersed with a humectant such as glycerine. Dental abrasive agents, including the anhydrous zeolite, surface-active agent and flavor are then separately added and uniformly dispersed. The toothpaste is then thoroughly deaerated (e.g., in vacuo) and tubed.

Preferably the amount of water-soluble essential flavoring oil is above 0.5% and below 2%. Strongly flavored toothpastes contain above about 1% of such flavoring oil, e.g., about 1.2 to 1.5%.

The following Examples are given to illustrate this invention further. In this application all proportions are by weight unless indicated.

EXAMPLE 1

Dental Cream

| Ingredients | % |
|---|---|
| Glycerin | 59.59 |
| Carbowax 600(polyethylene glycol of app. molecular weight of 600-Union Carbide) | 3.00 |
| Benzoic acid | 0.15 |
| Na₂PO₃F | 0.76 |
| Sodium zeolite 4A (anhydrous) | 30.00 |
| Silica aerogel (Syloid 244) | 4.00 |
| Sodium lauryl sulfate | 1.50 |
| Peppermint flavor | 1.00 |

The zeolite 4A was dried at 300° C. prior to incorporation into this composition.

The glycerin, carbowax, benzoic acid and the sodium monofluorophosphate are thoroughly mixed until uniform. The zeolite powder is added and mixed therewith until a uniform dispersion is obtained. The silica aerogel, sodium lauryl sulfate and flavor are each separately added to the mixture and each is thoroughly mixed until uniformly dispersed in the cream. The mixing process takes place in a low humidity room. This dental cream is packaged in the conventional manner.

The resultant product exhibits thermal effects when used in the brushing of teeth as well as a concurrent two tone flavor effect in the mouth, such as a burst of an initial flavor (cinnamon) which changes to another taste (mint) leaving a clean and refreshed feeling in the mouth and a feeling of smoothness on the teeth.

When 2 gms of this formulation are added to 1 ml water, the temperature rises from 72° F. to 87° F.; 2 gms of this dental cream plus 2 ml water effects a temperature rise from 72° F. to 88° F.

EXAMPLE 2

| Ingredient | Grams |
|---|---|
| Glycerin | 1203.0 |
| Carbowax 600 | 60 |
| Benzoic Acid | 3 |
| Saccharin | 4 |
| $Na_2PO_3F$ | 15.2 |
| Anhydrous Zeolite (4A) (Na) | 600 |
| Syloid 244 | 80 |
| Sodium Lauryl Sulfate | 30 |
| Flavor | 20 |

Packaged in pressurized container.
The same beneficial and unusual results are obtained.

EXAMPLE 3

| Ingredient | Grams |
|---|---|
| Glycerin | 1203 |
| Carbowax | 60 |
| Benzoic Acid | 3 |
| Saccharin | 4 |
| $Na_2PO_3F$ | 15.20 |
| "Calcium Zeolite" - dry (type 5A) | 600 |
| Syloid 244 | 80 |
| Sodium Lauryl Sulfate | 30 |
| Flavor | 20 |

Equally good results are obtained.
Ca zeolite 5A has the chemical formula:

$$Ca_{4.5}Na_3[(AlO_2)_{12}(SiO_2)_{12}]xH_2O,$$

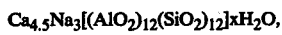

and will absorb molecules with critical diameters up to 5 angstroms, has a nominal pore diameter of 5 angstroms, a hydrated particle density of 2.03 g/cc, an activated particle density of 1.57 g/cc, an agglomerated particle diameter size of less than 10 microns with an average crystal size of 1.0 to 4.0 microns, and a maximum heat of adsorption of 1800 btu/lb $H_2O$, and an equilibrium $H_2O$ capacity of 28% weight.

The major physical difference between the 5A, the 4A and the 3A zeolites is in the critical pore diameter, which is 5, 4 and 3 angstroms respectively and can therefor absorb molecules with critical diameters up to 5, 4 and 3 respectively.

EXAMPLE 4

Example 2 is repeated except that the $Na_2PO_3F$ is omitted. The same unique two tone flavor and thermal effects is experienced while brushing your teeth therewith.

EXAMPLE 5

Example 1 is repeated, but zeolite 3A is used in lieu of 4A and the zeolite content is reduced to 10%, and 20% amorphous sodium alumino-silicate is added as the additional abrasive.

2 grams of the above plus 1 ml $H_2O$ effects a temperature rise from 72° F. to 76° F.

EXAMPLE 6

Example 5 is repeated, but the zeolite content is increased to 15% and the amorphous sodium alumino-silicate content is decreased to 15%.

2 grams of the above plus 1 ml $H_2O$ effects a temperature rise from 70° F. to 80° F.

EXAMPLE 7

Example 6 is repeated, but the zeolite content is reduced to 12.5% and the amorphous alumino-silicate content is increased to 17.5%.

2 grams of above product plus 1 ml $H_2O$ effects a temperature rise from 72° F. to 78° F.

EXAMPLE 8

Example 7 is repeated but zeolite 4A is used and the zeolite content is increased to 20% and the amorphous alumino-silicate content is reduced to 10%.

2 grams of the above product plus 1 ml $H_2O$ increases the temperature of the water from 70° F. to 82° F.

EXAMPLE 9

Example 8 is repeated but the zeolite content is increased to 25% and the amorphous alumino-silicate content is reduced to 5%.

2 grams of the above product plus 1 ml $H_2O$ raises the temperature of the water from 70° F. to 85° F.

EXAMPLE 10

Example 9 is repeated but zeolite 3A is used and its content is reduced to 5% and the amorphous aluminosilicate content is increased to 25%.

2 grams of this product plus $H_2O$ to liquify the product at 72° F. effects no increase in temperature, whereas 1 gm dried zeolite 3A plus water to suspend the zeolite resulted in a temperature rise from 72° F. to 88° F.

These examples clearly show that by increasing the amounts of zeolite in the dentifrice, a greater increase in the water temperature is obtained with a minimum temperature rise occurring with 10% zeolite. Accordingly, the dentifrice must contain a minimum of 10% zeolite and preferably 20–35% in order to achieve optimum results. It is also noted that all the zeolites, regardless of type, effect a similar elevation in the water temperature.

Other examples may be compounded wherein the flavor or flavors are changed to spearmint, eucalyptus, anethole, menthol, carvone, lemon, orange, etc., and the proportions varied over a 0.5 to 5% range, and preferably 0.5 to 2% for best taste effects.

Similarly, examples may be formulated wherein other surfactants such as sodium-N-lauroylsarcosinate and any of the other listed surfactants or mixtures thereof are substituted for the sodium lauryl sulfate, as well as other gelling agents, humectants or mixtures thereof.

The pH of the dentifrices is generally within the range of about 7 to 9.5.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:
1. An anhydrous heat releasing fluoride dentifrice which generates heat in the mouth enhancing the fluoride anticaries action and which effects a two tone fla- vor change in the oral cavity consisting of a finely divided anhydrous synthetic zeolite having an appreciable heat of hydration and capable of being reversibly dehydrated as the sole or major dental polishing agent in amounts of about 10 to 50% by weight which synthetic zeolite is a crystalline metal alumino silicate, said metal being selected from the group consisting of an alkali metal, alkaline earth metal, zinc, copper and mixtures thereof, an effective amount of a fluorine containing compound, about 0.1 to 5% by weight of at least one flavoring agent, and about 20 to 75% by weight of an anhydrous liquid vehicle.

2. A dentifrice according to claim 1, wherein the fluorine containing compound is selected from the group consisting of sodium fluoride and sodium monofluorophosphate in an amount of about 0.01 to 1% by weight of the water soluble fluorine content thereof.

3. A dentifrice according to claim 2, wherein the liquid vehicle is an anhydrous humectant or oil selected from the group consisting of glycerine, propylene glycol, polyethylene glycol, polypropylene glycol, liquid light petrolatum, mineral oil, vegetable oil, and suitable mixtures thereof.

4. A dentifrice in accordance with claim 3, which also includes about 0.5 to 10% of a gelling agent.

5. A dentifrice in accordance with claim 1, which additionally contains about 0.5 to 5% of a surface-active agent.

6. A dentifrice in accordance with claim 4, wherein the gelling agent is selected from the group consisting of sodium carboxymethyl cellulose, hydroxyethyl cellulose, polyvinyl alcohol, Irish moss, silica aerogel, and mixtures thereof.

7. A dentifrice according to claim 4, which also includes about 0.5 to 5% of a synthetic anionic surface-active agent.

8. A dentifrice in accordance with claim 7, which also contains a sweetening agent and wherein the flavoring agent is a flavoring oil in an amount of about 0.5 to 2% by weight.

* * * * *